(12) United States Patent
Zicherman

(10) Patent No.: US 6,290,669 B1
(45) Date of Patent: Sep. 18, 2001

(54) PERITONEAL DIALYSIS APPARATUS AND METHOD

(75) Inventor: Yehuda Zicherman, Bnei Brak (IL)

(73) Assignee: A.D.M. Advanced Dialysis Methods Ltd, Bnei Brak (IL)

( * ) Notice: Subject to any disclaimer, the term of this patent is extended or adjusted under 35 U.S.C. 154(b) by 0 days.

(21) Appl. No.: 09/341,854
(22) PCT Filed: Jan. 19, 1998
(86) PCT No.: PCT/IL98/00023
§ 371 Date: Jul. 20, 1999
§ 102(e) Date: Jul. 20, 1999
(87) PCT Pub. No.: WO98/32366
PCT Pub. Date: Jul. 23, 1998

(30) Foreign Application Priority Data

Jan. 24, 1997 (IL) .................................................. 120070

(51) Int. Cl.[7] ........................................................ A61M 1/00
(52) U.S. Cl. .............................................................. 604/29
(58) Field of Search ............................ 604/4, 5, 29, 241, 604/147; 128/DIG. 12

(56) References Cited

U.S. PATENT DOCUMENTS

| 4,657,160 | * | 4/1987 | Woods et al. | 604/141 |
| 5,147,310 | * | 9/1992 | Giannini et al. | 604/141 |
| 5,277,820 | * | 1/1994 | Ash | 604/4 |
| 5,336,165 | * | 8/1994 | Twardowski | 604/5 |
| 5,484,396 | * | 1/1996 | Naficy | 604/4 |

\* cited by examiner

Primary Examiner—Maxwel Mendez
(74) Attorney, Agent, or Firm—Benjamin J. Barish

(57) ABSTRACT

Peritoneal dialysis apparatus includes a holder device (11, 21, 31, 41, 51) for holding a container (10, 20, 30, 40, 50) of a dialysis fluid to be introduced into the peritoneal chamber (14, 24, 34, 44) of a subject; a catheter device (13, 23, 33, 43, 53) insertable through the abdominal wall (14a) of the subject for introducing the dialysis fluid into the peritoneal chamber (14, 24, 34, 44) for draining the dialysis fluid therefrom; and a conduit device (12, 22, 32, 42, 52) fluidly connecting a container (10, 20, 30, 40) held by the holder device (11, 21, 31, 41) to the catheter device (13, 23, 33, 43). The apparatus further includes an agitator (16, 25, 36, 45, 56, 57) cooperable with at least one of the above three devices for agitating the dialysis fluid in the peritoneal chamber (14, 24, 34, 44) in order to enhance the rate of solute removal therefrom.

31 Claims, 2 Drawing Sheets

PERITONEAL DIALYSIS APPARATUS AND METHOD

The present invention relates to peritoneal dialysis, particularly to apparatus and methods for enhancing the rate of solute removal during peritoneal dialysis.

Peritoneal dialysis (PD) is a medical treatment administered when there is insufficient functioning of the kidneys. It is performed by inserting a sterile plastic catheter into the abdominal cavity of the subject and instilling a dialysis fluid to irrigate the peritoneal chamber such that solutes transfer across the peritoneal membrane into the dialysis fluid from the blood in the mesentery capillary network. This treatment does not require a machine, such as in hemodialysis, but does require much longer periods of time in order to achieve solute removal comparable to that of intermittent hemodialysis. Such a treatment is commonly performed in an ambulatory manner as a CAPD (Continuous Ambulatory Peritoneal Dialysis) treatment.

CAPD is usually performed in four 6-hour sessions during each 24-hour period. In each session, the dialysis fluid is instilled into the peritoneal chamber of the subject and permitted to dwell therein for a period of six hours, following which the dialysis fluid is drained, and a fresh dialysis fluid is instilled. This relatively large number of sessions greatly disturbs the daily routine of the subject. It also increases the risk of infection.

Various studies have been conducted on the application of mechanical vibrations for improving the efficiency of waste removal by PD (peritoneal dialysis); see J.Rudoy et al. Nephron 46:364–366 (1987); Levitt et al. Kidney International, Vol. 35, pp. 1145–1150 (1989); Utsunomia-T et al., *Nippon-Jinzo-Gakkai-Shi;* 1995 Jan; 37(1):24–8; and Japanese Patent Application No. H2-2356561 by H.Aoki filed Sep. 7, 1990 and laid open Apr. 17, 1992, which discloses a peritoneal dialysis system in which low-frequency physical vibrations are applied to the abdomen during dialysis. My prior International Patent Application No. PCT/IL96/00064, filed Jul. 24, 1996 disclosed various appliances which included vibrator devices for applying localized, inwardly directed mechanical vibrations to the abdomen of the subject for this purpose.

An object of the present invention is to provide another type of peritoneal dialysis apparatus which can be used to enhance the rate of solute removal, or which can be used together with the peritoneal dialysis apparatus of my above International Patent Application in order to further enhance the rate of solute removal.

According to a broad aspect of the present invention, there is provided peritoneal dialysis apparatus, comprising a holder device for holding a container of a dialysis fluid to be introduced into the peritoneal chamber of a subject: a peritonial dialysis catheter device constructed to be insertable through the abdominal wall of the subject for introducing the dialysis fluid into the peritoneal chamber and for draining the dialysis fluid therefrom; and a conduit device fluidly connecting a container held by the holder device to the catheter device: characterized in that the apparatus further comprises an agitator located to be cooperable with at least one of said devices for agitating the dialysis fluid in the peritoneal chamber in order to enhance the rate of solute removal therefrom.

It will thus be seen that, whereas the apparatus of the above-identified patent application produced enhanced solute removal by applying mechanical vibrations to the subject's abdomen via an external vibrator, the apparatus of the present invention enhances solute removal by directly agitating the dialysis fluid in the peritoneal chamber of the subject. The apparatus of the present invention may be used in lieu of, but preferably is used with, that of my above International Patent Application in order to further enhance the rate of solute removal, and thereby to shorten the dialysis periods and/or to reduce the frequency of such periods.

A number of constructions are described below for purposes of example. In some constructions, the agitator is located to be cooperable with the holder device and acts on the container held thereby to agitate the dialysis fluid in the peritoneal chamber; in other constructions, the agitator is cooperable with the conduit device for agitating the dialysis fluid in the peritoneal chamber; and in still other constructions, the agitator is cooperable with the catheter device for agitating the dialysis fluid in the peritoneal chamber.

The invention also provides a method of peritoneal dialysis characterized in providing one of the above-mentioned devices with an agitator for agitating the dialysis fluid in the peritoneal chamber.

Further features and advantages of the invention will be apparent from the description below.

The invention is herein described, by way of example only, with reference to the accompanying drawings, wherein:

FIG. 1 schematically illustrates one embodiment of the present invention in the form of an apparatus having an agitator which is cooperable with the container holder device and acts on the container for agitating the dialysis fluid in the peritoneal chamber;

FIG. 2 schematically illustrates a second embodiment wherein the agitator is also cooperable with the holder device for the dialysis fluid container;

Figure 1:
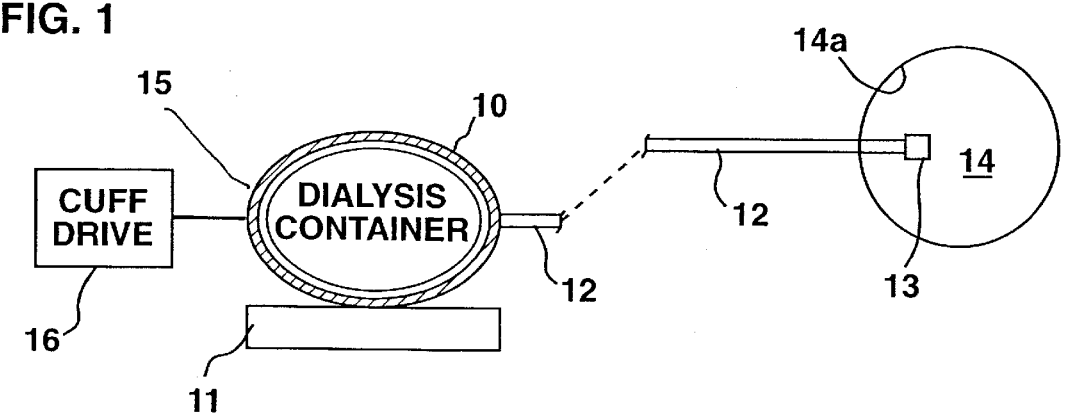

The apparatus illustrated in FIG. 1 includes a dialysis fluid container 10 supported on a holder 11 and connected via a conduit 12 to a catheter 13 inserted into the peritoneal chamber 14 of the subject via the abdominal wall 14a. In accordance with the present invention, the apparatus further includes an agitator which applies pulsations to the dialysis fluid in the peritoneal chamber of the subject in order to agitate the fluid therein and thereby to enhance the rate of solute removal therefrom.

In the apparatus illustrated in FIG. 1, these pulsations are applied by an inflatable-deflatable cuff 15 enclosing the dialysis fluid container 10 and periodically actuated via an actuator schematically indicated at 16 to expand and contract container 10 and thereby to agitate the dialysis fluid in the peritoneal chamber of the subject. Actuator 16 may be a pneumatic, hydraulic, or electrical actuator. Conduit 12 and catheter 13 may be a conventional flexible tube and catheter, respectively, as used in peritoneal dialysis systems.

Container 10 may be a pliable bag such as conventionally used in supplying fluids for peritoneal dialysis. In such case, its holder 11 would normally be below the level of the catheter 13 so that inflation of the cuff pumps the fluid from the bag towards the subject's peritoneal chamber, whereas deflation of the cuff permits the fluid to drain by gravity in the reverse direction. Container 10, however, could also be a plastic pinch-bottle, such that inflation and deflation of the cuff cause contraction and expansion of the bottle to produce the agitation of the dialysis fluid in the subject's peritoneal chamber. Cuff 15 is inflated and deflated during the dwell phase of the dialysis fluid within the subject's peritoneal chamber, but could also be controlled to pump the fluid into, and/or out of, the peritoneal chamber during the instillation and removal phases.

Figure 2:
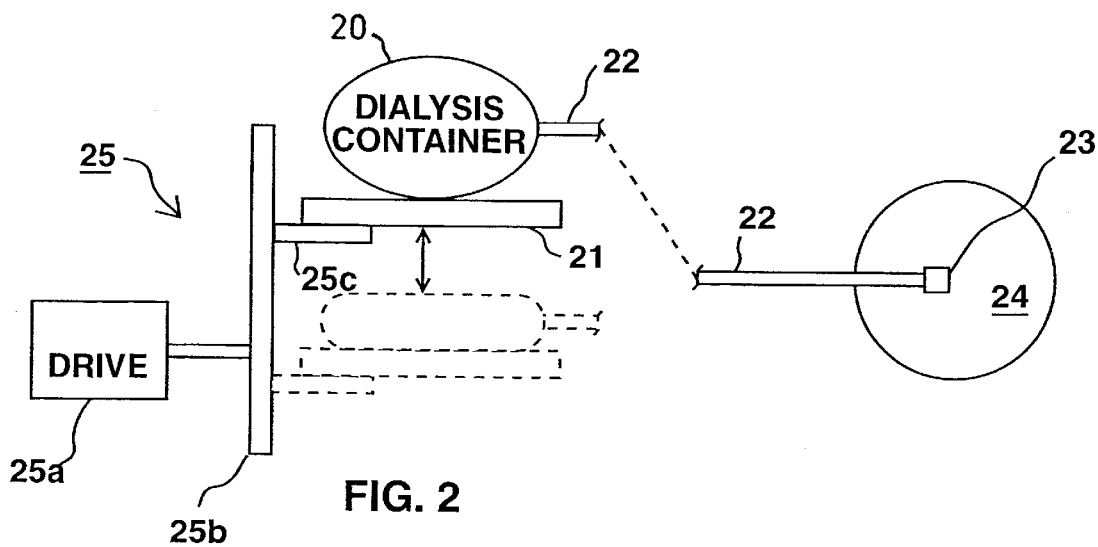

FIG. 2 illustrates another constructions, wherein the dialysis fluid container 20 supported on a holder 21 also feeds dialysis fluid via a tubing type conduit 22 to a catheter 23 within the peritoneal chamber 24 of the subject. In this case, the dialysis fluid container 20 is periodically agitated by a raising and lowering device, generally designated 25, for periodically raising and lowering the dialysis fluid container 20 above and below the level of the catheter. The raising and lowering device 25 in FIG. 2 is schematically illustrated as including a motor 25a driving a rotary disk 25b and an eccentric mounting 25c on disk 25 for the container holder 21. Other devices may be used for this purpose, for example a screw and nut mechanism rotated by an electrical motor.

Figure 3:
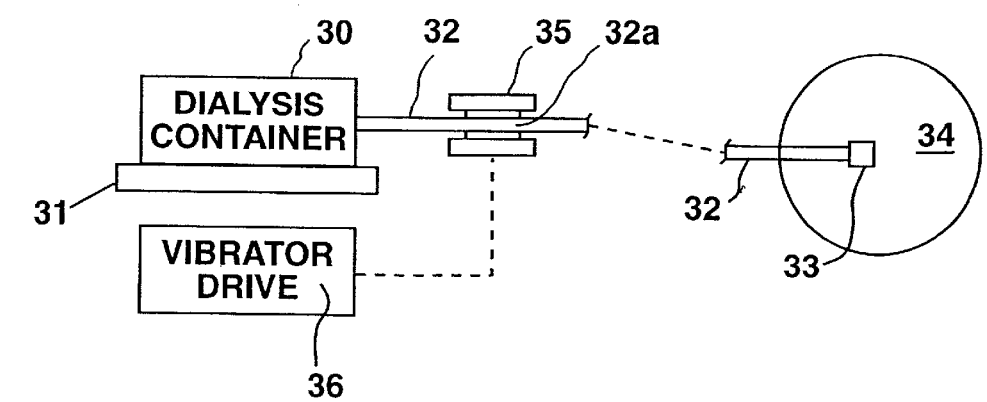
FIG. 3 illustrates a third embodiment wherein the agitator is cooperable with the conduit feeding the dialysis fluid to the catheter.

FIG. 3 illustrates another arrangement, wherein the dialysis fluid container 30 is supported on a holder 31 and is fed via tubing 32 and catheter 33 into the subject's peritoneal chamber 34, but in this case the agitator is in the form of an external vibrator 35 acting on section 32a of the tubing 32 and driven by a vibrator drive 36. Thus, during the instillation phase, holder 31 would be located above the level of the catheter 33 so as to feed the dialysis fluid by gravity, during which time the external vibrator 35 could be actuated to produce fluctuations or pulsations in the fluid as it is fed into the peritoneal chamber. The vibrator could raise and lower section 32a of tubing 32 in order to produce the fluctuations during the dwell phase. Alternatively, during the dwell phase the container 30 could be raised and lowered with respect to the level of the catheter 33, and vibrator 35 could be used to open and pinch-close section 32a of the tubing. For draining the fluid from the peritoneal chamber, holder 31 would be lowered below the catheter 33, and preferrably vibrator 35 would not be actuated.

Figure 4:
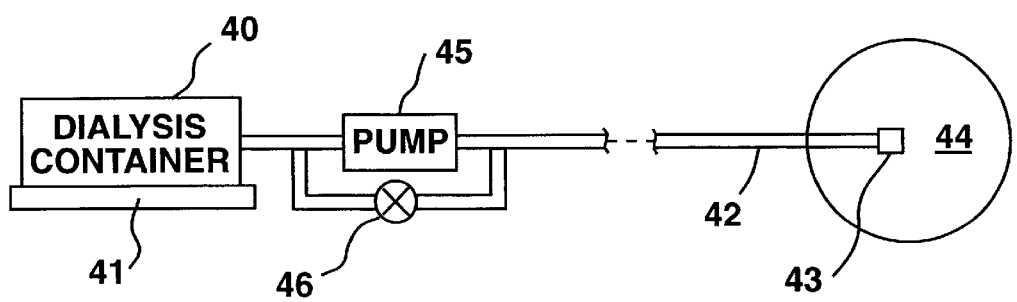
FIG. 4 illustrates a fourth embodiment wherein the agitator is also cooperable with the conduit feeding the dialysis fluid to the catheter.

FIG. 4 illustrates an arrangement which also includes a dialysis container 40 supported on a holder 41 and feeding the dialysis fluid via tubing 42 to the catheter 43 within the subject's peritoneal chamber 44. In this case, however, instead of having the dialysis fluid gravity-fed as in FIG. 3, the dialysis fluid is fed via a pump 45. Pump 45 is preferrably of a type which alternately produces positive and negative pressure outputs so as to agitate the fluid within tubing 42 and the peritoneal chamber 44. Alternatively, the dialysis container 40, e.g. a conventional bag, could be held by holder 41 below the level of the catheter 43, and the pump 45 could be periodically actuated to pump the fluid towards the peritoneal chamber 44, whereby the fluid would flow in the reverse direction by gravity during the periods between pump actuations. In order to prevent internal damage by an excesive pressure, a relief valve 46 is provided that opens a bypass around the pump when the pressure produced by the pump is too high.

Figure 5:
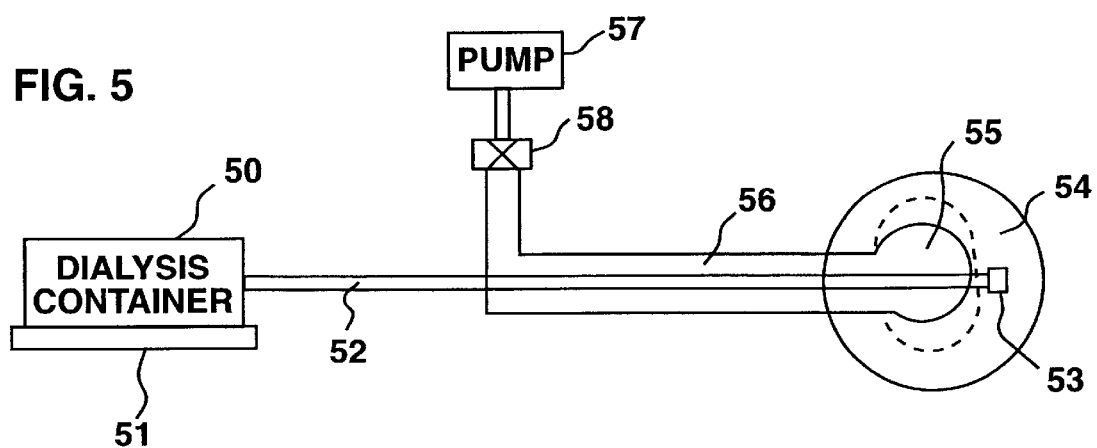
FIG. 5 illustrates a fifth embodiment wherein the agitator is cooperable with the catheter for agitating the dialysis fluid in the peritoneal chamber.

FIG. 5 illustrates another arrangement wherein the agitations are produced at the catheter end of the dialysis fluid delivery system. Thus, FIG. 5 illustrates the dialysis fluid container 50 on a holder 51 and feeding the dialysis fluid via tubing 52 and catheter 53 into the peritoneal chamber 54 of the subject. Tubing 52 thus serves as a first lumen for feeding the dialysis fluid to catheter 53. The illustrated apparatus includes an inflatable bag 55 introduced into the peritoneal chamber of the subject with the catheter 53, and a second lumen 56 operated by pump 57 and controlled by valve 58 for alternately inflating and deflating bag 55. Thus, lumen 52 passes through the inflatable bag 55 and is used for dialysate instillation and drainage as in a conventional peritoneal dialysis system. Lumen 56, which encloses lumen 52, is used for pumping a fluid (air or liquid) in order to alternately inflate and deflate bag 55, and thereby to agitate the dialysis fluid within the peritoneal chamber for enhancing the rate of solute removal therefrom.

In the constructions described above, the method of agitating the dialysis fluid in the subject's peritoneal chamber will not be unduly disturbing to the subject, and therefore the procedure could be applied in most cases while the patient is asleep. As indicated above, the described method may be used in addition to, or in lieu of, the method described in my above-cited International Patent Application involving the actuation of an external vibrator for vibrating the subject's abdomen.

The method of the present invention could also be used in a Continuous Cyclic Peritoneal Dialysis (CCPD) treatment, which is similar to a Continuous Automated Peritoneal Dialysis (CAPD) treatment except that a machine called a cycler is connected to the catheter to automatically fill and drain the dialysate from the abdomen. Such a treatment is generally performed at night and exchanges the dialysate 4–8 times. Because of the inadequacy of this method, 1–2 daily CAPD treatments are added occasionally to the night routine. Adding a vibrating device in accordance with the present invention is expected to increase the efficiency of APD by applying vibrations through the fluid that fills the cycler's tubing set, and thereby to reduce the need to exchange fluid throughout the day.

While the invention has been described with respect to several preferred embodiments, it will be appreciated that these are set forth merely for purposes of example, and that many other variations, modifications and applications of the invention may be made.

What is claimed is:

1. Peritoneal dialysis apparatus, comprising:
   a holder device for holding a container of a dialysis fluid to be introduced into the peritoneal chamber of a subject:
   a peritoneal dialysis catheter device constructed to be insertable through the abdominal wall of the subject to introduce the dialysis fluid into the peritoneal chamber and to drain the dialysis fluid therefrom;
   and a conduit device fluidly connecting a container held by said holder device to said catheter device:
   characterized in that said apparatus further comprises an agitator located to be cooperable with at least one of said devices for agitating the dialysis fluid in the peritoneal chamber in order to enhance the rate of solute removal therefrom.

2. The apparatus according to claim 1, wherein said agitator is located to be cooperable with said holder device and acts on the container held thereby to agitate the dialysis fluid in the peritoneal chamber.

3. The apparatus according to claim 2, wherein said agitator includes an inflatable-deflatable cuff to expand and contract the container and thereby to agitate the dialysis fluid in the peritoneal chamber.

4. The apparatus according to claim 2, wherein said agitator includes a raising and lowering device to raise and lower the container holder device and thereby to agitate the dialysis fluid in the peritoneal chamber.

5. The apparatus according to claim 1, wherein said agitator is located to be cooperable with the conduit device for agitating the dialysis fluid in the peritoneal chamber.

6. The apparatus according to claim 5, wherein said agitator includes a vibrator acting on the conduit device for agitating the dialysis fluid in the peritoneal chamber.

7. The apparatus according to claim 6, wherein said vibrator raises and lowers a section of the conduit device for agitating the dialysis fluid in the peritoneal chamber.

8. The apparatus according to claim 6, wherein said vibrator opens and closes a section of the conduit device for agitating the dialysis fluid in the peritoneal chamber.

9. The apparatus according to any one of claims 2–8, wherein said dialysis fluid is gravity fed through the conduit device.

10. The apparatus according to claim 1, wherein said agitator includes a pump for pumping the fluid in the form of pulses from the container to the catheter device.

11. The apparatus according to claim 10, wherein said pump produces alternate pressure and suction outputs to alternately pump the dialysis fluid towards the peritoneal chamber and to draw the dialysis fluid from the peritoneal chamber.

12. The apparatus according to claim 10, wherein said holder device holds the container at a level below that of the peritoneal dialysis catheter device, and wherein said pump is periodically actuated to pump the dialysis fluid towards the peritoneal chamber, the dialysis fluid flowing in the reverse direction by gravity during the periods between the actuations of the pump.

13. The apparatus according to any of claims 10–12, wherein said apparatus further includes includes a relief valve bypassing the fluid around the pump when the pressure of the fluid exeeds a predetermined maximum positive or negative pressure.

14. The apparatus according to claim 1, wherein said agitator is located to be cooperable with the peritoneal dialysis catheter device for agitating the dialysis fluid in the peritoneal chamber.

15. The apparatus according to claim 14, wherein said peritoneal dialysis catheter device includes:

a catheter to be inserted into the subject's peritoneal chamber;

a first lumen for feeding the dialysis fluid to or from said catheter;

an inflatable bag introduced with said catheter into the peritoneal chamber of the subject;

and a second lumen for inflating and deflating said inflatable bag.

16. The apparatus according to claim 15, wherein said first lumen passes through said inflatable bag.

17. A method of peritoneal dialysis by introducing dialysis fluid into the peritoneal chamber of a subject via a container of the dialysis fluid held by a holder device, a peritoneal dialysis catheter device constructed to be insertable into the abdominal wall of the subject, and a conduit device fluidly connecting the container to the catheter device; characterized in providing at least one of said devices with an agitator for agitating the dialysis fluid in the peritoneal chamber.

18. The method according to claim 17, wherein said agitator is provided on said holder device and acts on the container held thereby to agitate the dialysis fluid in the peritoneal chamber.

19. The method according to claim 18, wherein said agitator includes an inflatable-deflatable cuff to expand and contract the container and thereby to agitate the dialysis fluid in the peritoneal chamber.

20. The method according to claim 18, wherein said agitator raises and lowers the container holder device and thereby agitates the dialysis fluid in the peritoneal chamber.

21. The method according to claim 17, wherein said agitator is provided on said conduit device to agitate the dialysis fluid in the peritoneal chamber.

22. The method according to claim 21, wherein said agitator vibrates a section of the conduit device to agitate the dialysis fluid in the peritoneal chamber.

23. The method according to claim 22 wherein said vibrator raises and lowers a section of the conduit device for agitating the dialysis fluid in the peritoneal chamber.

24. The method according to claim 22, wherein said vibrator opens and closes a section of the conduit device for agitating the dialysis fluid in the peritoneal chamber.

25. The method according to any one of claims 18–24, wherein said dialysis fluid is gravity fed through the conduit device.

26. The method according to claim 17, wherein said agitator includes a pump for pumping the fluid in the form of pulses from the container to the catheter device.

27. The method according to claim 26, wherein said pump produces alternate pressure and suction outputs to alternately pump the dialysis fluid towards the peritoneal chamber and to draw the dialysis fluid from the peritoneal chamber.

28. The method according to claim 26, wherein said holder device holds the container at a level below that of the catheter device, and wherein said pump is periodically actuated to pump the dialysis fluid towards the peritoneal chamber, the dialysis fluid flowing in the reverse direction by gravity during the periods between the actuations of the pump.

29. The method according to any one of claims 26–28, wherein a relief valve bypasses the fluid around the pump when the pressure of the fluid exeeds a predetermined maximum.

30. The method according to claim 17, wherein said agitator is cooperable with the catheter device for agitating the dialysis fluid in the peritoneal chamber.

31. The method according to claim 30, wherein an inflatable bag introduced with said catheter device into the peritoneal chamber of the subject is periodically inflated and deflated.

* * * * *